US00PP15262P2

(12) United States Plant Patent
van Straalen et al.

(10) Patent No.: US PP15,262 P2
(45) Date of Patent: Oct. 26, 2004

(54) *ASTER* PLANT NAMED 'DYNASTER'

(50) Latin Name: *Aster novi-belgii*
Varietal Denomination: Dynaster

(75) Inventors: Harry W. M. van Straalen, Rijsenhout (NL); Wilfried J. Poland, Wervershoof (NL)

(73) Assignee: Chrysanthemum Breeders Association N.V. (NL)

( * ) Notice: Subject to any disclaimer, the term of this patent is extended or adjusted under 35 U.S.C. 154(b) by 18 days.

(21) Appl. No.: 10/426,849

(22) Filed: May 1, 2003

(51) Int. Cl.[7] ..... A01H 5/00
(52) U.S. Cl. ..... Plt./355
(58) Field of Search ..... Plt./355

*Primary Examiner*—Bruce R. Campell
*Assistant Examiner*—Michelle Kizilkaya
(74) *Attorney, Agent, or Firm*—Parkhurst & Wendel, L.L.P.

(57) ABSTRACT

An *Aster* plant named 'Dynaster' characterized by its medium sized blooms with violet-blue ray-florets and yellow disc florets, which can be propagated by means of cuttings from cuttings and produced within a short period.

3 Drawing Sheets

Scientific name of the plant: *Aster novi-belgii* L. 'Dynaster'.

RELATED CULTIVARS

'Dynaster' is related to 'Diamaster' (copending U.S. Plant patent application Ser. No. 10/426,847) and 'Dukaster' (copending U.S. Plant patent application Ser. No. 10/426,848), which are all *aster* varieties developed from similar breeding programs.

BACKGROUND OF THE INVENTION

'Dynaster' is a product of a breeding-program that had the objective of creating new *Aster* cultivars, which can be grown as pot plants and propagated by means of cuttings from cuttings, similar to the cultivation and propagation of all year round pot chrysanthemum. The new plant of the present invention comprises a new and distinct cultivar of an *Aster* plant. 'Dynaster' is a seedling from a cross in a breeding program maintained under the control of the inventor. The female parent is an unnamed seedling not available to the inventor for description. The male parent is unknown, being a mixed population of a group of male parents. To the inventor's knowledge, neither the female nor male parents are patented. The new and distinct cultivar was discovered and selected as a flowering plant within the progeny of the stated cross by Harry W. M. van Straalen in a controlled environment (greenhouse) in Rijsenhout, Holland in 1995. The first act of asexual reproduction of 'Dynaster' was accomplished when vegetative cuttings were taken from the initial selection in 1999 in a controlled environment in Rijsenhout, Holland.

SUMMARY OF THE INVENTION

The present invention is a new and distinct variety of *Aster* bearing medium sized blooms with violet-blue ray-florets and yellow disc florets, which can be propagated by a cutting from a cutting and need 8 weeks to produce flowering pot plants.

BRIEF DESCRIPTION OF THE DRAWINGS

The present invention of a new and distinct variety of *Aster* is shown in the accompanying drawings, the color being as nearly true as possible with color photographs of this type.

Figure 1:
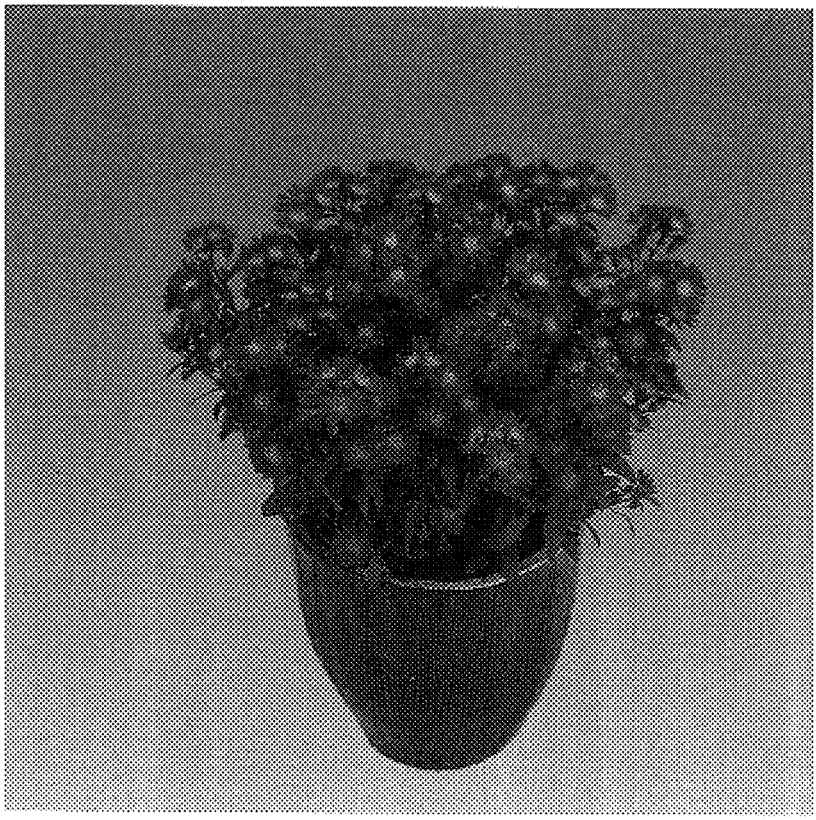
FIG. 1 shows a plant of the cultivar in full bloom.
Figure 2:
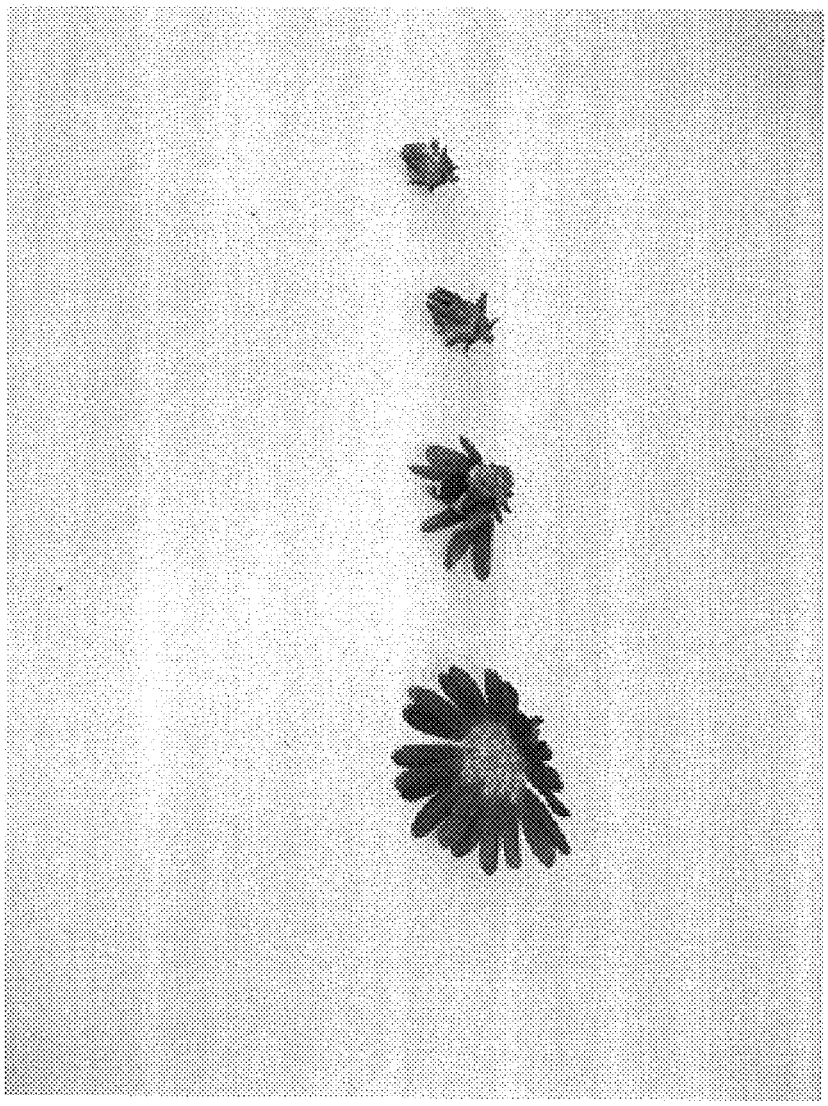
FIG. 2 shows the various stages of bloom of the new cultivar.
Figure 3:
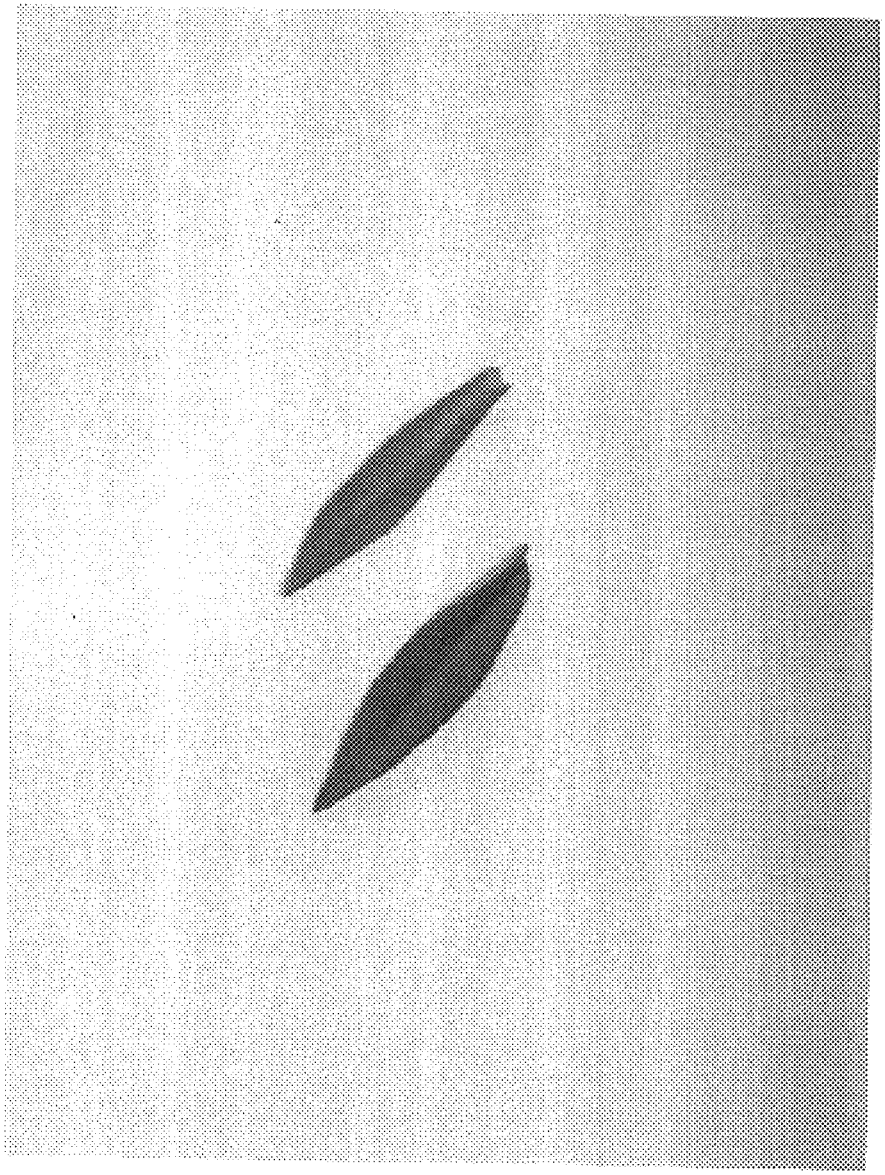
FIG. 3 shows the foliage of the new cultivar.

The drawings are photographs of a 9-week old plant, cultivated as further described herein.

DESCRIPTION OF THE INVENTION

This new variety of *Aster* is of the botanical classification *Aster novi-belgii* L. The observations and measurements were gathered from plants grown in a greenhouse in Rijsenhout, Holland in a photo-periodic controlled crop under conditions generally used in commercial practice. The greenhouse temperatures during this crop were at day-time between 18° C. and 25° C. and at night 20° C. The photo-periodic response time in this crop was 39 days after an average of sixteen long days after sticking of the unrooted cuttings. Plants were pinched ten days after sticking. Growth retardants were applied in an average dose of 1.5 gram/liter water, starting one week after pinching. The plants were observed (directly) during the flowering of this crop. The plant is susceptible to Powdery Mildew. No tests were done on cold or drought tolerance. This new variety produces medium sized blooms with violet-blue ray-florets and yellow disc-florets blooming on the plant for 4 weeks. This new variety of *Aster* has been found to retain its distinctive characteristics throughout successive propagations; however, the phenotype may vary significantly with variations in environment such as light intensity and temperature. 'Dynaster' can be planted with assimilation lightning (high pressure sodium lamps) between week 5 and week 35 under greenhouse conditions in Holland.

From the cultivars known to inventor the most similar existing cultivar in comparison to 'Dynaster' is 'Dasfour' (U.S. Plant Pat. No. 11,451) When 'Dasfour' and 'Dynaster' are being compared the following differences are noticed: The difference of 'Dasfour' and 'Dynaster' are (1) Method of propagation. (2) Production time (3) Size of bloom. (4) Color of ray-florets. (1) In the propagation of 'Dasfour', motherplants for the production of cuttings originate from in-vitro material, while in the case of 'Dynaster' motherplants can be directly obtained as cuttings from cuttings. (2) The total time needed to obtain flowering time is different, for 'Dasfour' this is 13 weeks while for 'Dynaster' this amounts to 8 weeks. (3) The size of the bloom of 'Dasfour' is larger than that of 'Dynaster'. (4) 'Dasfour' and 'Dynaster' have both blue-purple colored ray-florets, but those of 'Dasfour' are more purple colored than the ones from 'Dynaster'.

'Dynaster' differs from 'Diamaster' and 'Dukaster' in flowering response time, flower size, and ray-floret color. The following response time of 'Diamaster' is 42 days, while the flowering response time of 'Dukaster' and 'Dynaster' is 39 days. The flower size of 'Diamaster' is small, while the flower size of 'Dukaster' and 'Dynaster' is medium. The 'Diamaster' ray-florets are white, while the ray-florets of 'Dukaster' are pink and the ray-florets of 'Dyanster' are violet-blue.

The following is a description of the plant and characteristics that distinguish 'Dynaster' as a new and distinct variety.

The color descriptions are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of Cultivar 'Dynaster'

Bud:
- *Size.*—Medium; cross-section 0.4 cm, height 0.6 cm.
- *Outside color.*—Violet-blue 90 D.
- *Involucral bracts.*—2 rows, length 4 mm, width 3 mm.
- *Involucral bracts among disc-florets.*—Not present.
- *Involucral bracts color.*—Green 138 C.

Bloom:
- *Type.*—Daisy.
- *Size.*—Small-medium.
- *Fully expanded.*—3.5 cm.
- *Number of blooms per branch.*—11.
- *Peduncle length.*—2.5 cm.
- *Peduncle color.*—Green 139 B with streaks of Greyed-purple 186 B.
- *Peduncle, angle to stem.*—30°.
- *Performance on the plant.*—4 weeks.
- *Seeds.*—Produced in small quantities, oval/ovate shaped, grey-brown 199 A, 1 mm. in length.

Color:
- *Center of the flower* (*disc-florets*).—Immature Yellow-green 151 A. Mature Yellow 1 A.
- *Color of the ray-florets.*—Upper surface: Violet-blue 90 A. Lower surface: Violet-blue 90 D.
- *Tonality from distance.*—A pot *aster* with violet-blue flowers and a yellow disc.
- *Color of the surface of the ray-florets after aging of the plant.*—Violet-blue 90 C.

Ray florets:
- *Number of whorls of ray-florets.*—2.
- *Texture.*—Upper and under side smooth.
- *Number of ray-florets.*—20.
- *Shape in cross-section.*—Straight.
- *Curvature of longitudinal axis.*—Flat.
- *Length of corolla tube.*—0.4 cm.
- *Length.*—1.6 cm.
- *Width.*—0.2 cm.
- *Shape of tip.*—Pointed.
- *Shape of apex.*—Acute.

Disc florets:
- *Disc diameter.*—0.9 cm.
- *Distribution of disc florets.*—Numerous, clearly visible at all stages of flowering.
- *Shape.*—Funnel.
- *Lenght.*—0.8 cm.
- *Color.*—Yellow-green 145 D.

Reproductive organs:
- *Stamen.*—Present; very small amount in disc-florets only.
- *Stamen color.*—Yellow-green 144 B.
- *Pollen.*—Present.
- *Pollen color.*—Yellow-orange 14 A.
- *Styles.*—Ppresent in both ray and disc-florets.
- *Style color.*—Yellow-green 150 D.
- *Style length.*—0.8 cm.
- *Ovaries.*—Enclosed in calyx.
- *Calyx shape.*—Pappus.
- *Calyx lenght.*—0.5 cm.
- *Calyx color.*—Yellow-green 150 D.

Plant:
- *Form.*—A pot *aster* meant for indoor use.
- *Growth habit.*—Upright growing.
- *Growth rate.*—Vigorous.
- *Height.*—22 cm.
- *Width.*—7.5 cm.
- *Internode lenght.*—1.5 cm.
- *Stem diameter.*—2 mm.
- *Stem color.*—Green 139 B with streaks of Greyed-purple 186 B.
- *Stem strength.*—Strong.
- *Stem brittleness.*—Not brittle.
- *Stem anthocyanin coloration.*—Present.
- *Length of lateral branch.*—From top to bottom 15 cm.
- *Lateral branch color.*—Green 139 B.
- *Lateral branch, attachment.*—25°.
- *Branching* (*average number of lateral branches*).—Good with 3 breaks after pinching.
- *Flowering response* (*photo-periodic controlled crop, not natural season.*—39 ays.

Foliage:
- *Leaf arrangement.*—Alternate.
- *Color immature stage.*—Upper side Yellow-green 144 B. Under side Yellow-green 146 C.
- *Color mature stage.*—Upper side Green 137 B. Under side Green 137 C.
- *Color midvein.*—Upper side Green 138B with Greyed-purple 186 B. Under side Green 138 B.
- *Size.*—Medium; length 6 cm, width 1.5 cm.
- *Quantity* (*number per lateral branch*).—12–14.
- *Shape.*—Lanceolate.
- *Texture upper side.*—Glabrous.
- *Texture under side.*—Glabrous.

*Venation arrangement.*—Pinnately netted.
*Shape of the margin.*—Sinuate.
*Shape of base.*—Attenuate.
*Apex.*—Acuminate.

Differences with the comparison varieties

| | 'Dynastek' | 'Dasfour' |
|---|---|---|
| Propagation | Cuttings from cuttings | In-vitro cycle necessary |
| Production time | 8 weeks | 13 weeks |
| Size bloom | Small to Medium | Medium |

-continued

Differences with the comparison varieties

| | 'Dynastek' | 'Dasfour' |
|---|---|---|
| Color upperside ray-florets | Violet-blue 90A | Purple 77A |

I claim:

1. A new and distinct variety of *Aster* plant as described and illustrated.

* * * * *